United States Patent
Ebner (10) Patent No.: US 8,500,776 B2
(45) Date of Patent: Aug. 6, 2013

(54) VACUUM PATCH FOR RAPID WOUND CLOSURE

(75) Inventor: Timothy D. Ebner, New Haven, CT (US)

(73) Assignee: Covidien LP, Mansfield, MA (US)

(*) Notice: Subject to any disclaimer, the term of this patent is extended or adjusted under 35 U.S.C. 154(b) by 201 days.

(21) Appl. No.: 12/987,264

(22) Filed: Jan. 10, 2011

(65) Prior Publication Data

US 2011/0196420 A1      Aug. 11, 2011

Related U.S. Application Data

(60) Provisional application No. 61/302,269, filed on Feb. 8, 2010.

(51) Int. Cl.
*A61B 17/08* (2006.01)

(52) U.S. Cl.
USPC ......... 606/213; 606/151; 606/215; 623/23.72

(58) Field of Classification Search
None
See application file for complete search history.

(56) References Cited

U.S. PATENT DOCUMENTS

| | | |
|---|---|---|
| 2,513,771 A | 7/1950 | Williams |
| 2,671,444 A | 3/1954 | Pease, Jr. |
| 3,054,406 A | 9/1962 | Usher |
| 4,347,847 A | 9/1982 | Usher |
| 4,452,245 A | 6/1984 | Usher |
| 4,705,040 A | 11/1987 | Mueller et al. |
| 4,741,330 A | 5/1988 | Hayhurst |
| 4,854,316 A | 8/1989 | Davis |
| 4,865,031 A | 9/1989 | O'Keeffe |
| 5,041,129 A | 8/1991 | Hayhurst et al. |
| 5,053,046 A | 10/1991 | Janese |
| 5,171,259 A * | 12/1992 | Inoue ............... 606/213 |
| 5,246,455 A | 9/1993 | Shikani |
| 5,254,133 A | 10/1993 | Seid |
| 5,304,117 A | 4/1994 | Wilk |
| 5,350,399 A * | 9/1994 | Erlebacher et al. ...... 606/213 |
| 5,366,460 A | 11/1994 | Eberbach |
| 5,370,650 A | 12/1994 | Tovey et al. |
| 5,391,182 A | 2/1995 | Chin |
| 5,474,573 A | 12/1995 | Hatcher |

(Continued)

FOREIGN PATENT DOCUMENTS

| | | |
|---|---|---|
| EP | 166721 A2 | 1/2002 |
| EP | 2253276 A1 | 11/2010 |
| WO | WO 00/18301 A1 | 4/2000 |
| WO | WO 2007/016261 * | 2/2007 ............ 606/213 |

OTHER PUBLICATIONS

European Search Report for corresponding EP11250141 date of mailing is Jul. 1, 2011 (3 pages).

*Primary Examiner* — Corrine M McDermott
*Assistant Examiner* — Todd J Scherbel (57) ABSTRACT

A surgical patch system for closing a wound includes a first surgical patch, a second surgical patch, a cord operably associated with the first and second surgical patches, and a port operably associated with the second surgical patch. The first surgical patch is positionable adjacent internal tissue of an underlying tissue site of an open wound. The second surgical patch is positionable adjacent external tissue relative to the underlying tissue site of the open wound. The external tissue is adjacent the internal tissue. The cord is configured and dimensioned to interconnect the first and second surgical patches. The port is positioned to enable the application of negative pressure to the open wound.

18 Claims, 8 Drawing Sheets

U.S. PATENT DOCUMENTS

| | | | |
|---|---|---|---|
| 5,507,755 | A | 4/1996 | Gresl et al. |
| 5,507,811 | A | 4/1996 | Koike et al. |
| 5,578,045 | A | 11/1996 | Das |
| 5,707,393 | A | 1/1998 | Kensey et al. |
| 5,861,003 | A | 1/1999 | Latson et al. |
| 5,879,366 | A | 3/1999 | Shaw et al. |
| 5,899,911 | A | 5/1999 | Carter |
| 5,916,225 | A | 6/1999 | Kugel |
| 5,944,738 | A | 8/1999 | Amplatz et al. |
| 5,972,008 | A | 10/1999 | Kalinski et al. |
| D416,327 | S | 11/1999 | Kugel |
| 6,010,447 | A | 1/2000 | Kardjian |
| 6,045,551 | A | 4/2000 | Bonutti |
| 6,080,168 | A | 6/2000 | Levin et al. |
| 6,080,182 | A | 6/2000 | Shaw et al. |
| 6,080,194 | A | 6/2000 | Pachence et al. |
| 6,117,160 | A | 9/2000 | Bonutti |
| 6,174,320 | B1 | 1/2001 | Kugel et al. |
| 6,176,863 | B1 | 1/2001 | Kugel et al. |
| 6,214,029 | B1 | 4/2001 | Thill et al. |
| 6,224,616 | B1 | 5/2001 | Kugel |
| 6,238,395 | B1 | 5/2001 | Bonutti |
| 6,241,768 | B1 | 6/2001 | Agarwal et al. |
| 6,258,124 | B1 | 7/2001 | Darois et al. |
| 6,280,453 | B1 | 8/2001 | Kugel et al. |
| 6,312,442 | B1 | 11/2001 | Kieturakis et al. |
| 6,352,543 | B1 | 3/2002 | Cole |
| 6,383,201 | B1 | 5/2002 | Dong |
| 6,391,059 | B1 | 5/2002 | Lemperle et al. |
| 6,398,796 | B2 | 6/2002 | Levinson |
| 6,425,924 | B1 | 7/2002 | Rousseau |
| 6,508,828 | B1 | 1/2003 | Akerfeldt et al. |
| 6,551,303 | B1 * | 4/2003 | Van Tassel et al. ............ 604/508 |
| 6,626,930 | B1 | 9/2003 | Allen et al. |
| 6,635,073 | B2 | 10/2003 | Bonutti |
| 6,638,312 | B2 | 10/2003 | Plouhar et al. |
| 6,669,707 | B1 | 12/2003 | Swanstrom et al. |
| 6,669,713 | B2 | 12/2003 | Adams |
| 6,679,900 | B2 | 1/2004 | Kieturakis et al. |
| 6,726,705 | B2 | 4/2004 | Peterson et al. |
| 6,764,500 | B1 | 7/2004 | Muijs Van De Moer et al. |
| 6,790,213 | B2 | 9/2004 | Cherok et al. |
| 6,800,082 | B2 | 10/2004 | Rousseau |
| 6,932,827 | B2 | 8/2005 | Cole |
| 6,966,916 | B2 | 11/2005 | Kumar |
| 7,021,316 | B2 | 4/2006 | Leiboff |
| 7,044,982 | B2 | 5/2006 | Milbocker |
| 7,101,381 | B2 * | 9/2006 | Ford et al. ...................... 606/151 |
| 7,169,168 | B2 | 1/2007 | Muijs Van De Moer et al. |
| 7,338,514 | B2 * | 3/2008 | Wahr et al. ..................... 606/213 |
| 7,576,257 | B2 | 8/2009 | LaGreca, Sr. |
| 7,594,921 | B2 | 9/2009 | Browning |
| 7,842,069 | B2 * | 11/2010 | Widomski et al. ............ 606/213 |
| 8,029,522 | B2 * | 10/2011 | Ortiz et al. ..................... 606/155 |
| 8,177,809 | B2 * | 5/2012 | Mavani et al. ................. 606/213 |
| 8,292,917 | B2 * | 10/2012 | Chopra .......................... 606/213 |
| 2001/0049539 | A1 | 12/2001 | Rehil |
| 2001/0051815 | A1 | 12/2001 | Esplin |
| 2002/0026159 | A1 | 2/2002 | Zhu et al. |
| 2002/0049503 | A1 | 4/2002 | Milbocker |
| 2002/0065494 | A1 | 5/2002 | Lockwood et al. |
| 2002/0068950 | A1 | 6/2002 | Corcoran et al. |
| 2002/0103494 | A1 | 8/2002 | Pacey |
| 2003/0055455 | A1 | 3/2003 | Yang et al. |
| 2003/0194505 | A1 | 10/2003 | Milbocker |
| 2004/0049210 | A1 | 3/2004 | VanTassel et al. |
| 2004/0049211 | A1 | 3/2004 | Tremulis et al. |
| 2004/0092969 | A1 | 5/2004 | Kumar |
| 2004/0093027 | A1 | 5/2004 | Fabisiak et al. |
| 2005/0222544 | A1 | 10/2005 | Weston |
| 2005/0256532 | A1 * | 11/2005 | Nayak et al. .................. 606/151 |
| 2005/0261642 | A1 | 11/2005 | Weston |
| 2006/0025785 | A1 | 2/2006 | Cully et al. |
| 2006/0089671 | A1 | 4/2006 | Goldfarb et al. |
| 2006/0142797 | A1 | 6/2006 | Egnelov |
| 2007/0185506 | A1 | 8/2007 | Jackson |
| 2007/0260179 | A1 | 11/2007 | Sholev et al. |
| 2007/0260268 | A1 | 11/2007 | Bartee et al. |
| 2008/0033461 | A1 | 2/2008 | Koeckerling et al. |
| 2008/0071310 | A1 | 3/2008 | Hoffman et al. |
| 2008/0091222 | A1 | 4/2008 | Deusch et al. |
| 2008/0091235 | A1 | 4/2008 | Sirota |
| 2008/0097489 | A1 | 4/2008 | Goldfarb et al. |
| 2008/0114395 | A1 | 5/2008 | Mathisen et al. |
| 2008/0119877 | A1 | 5/2008 | Deusch et al. |
| 2008/0119878 | A1 | 5/2008 | Deusch et al. |
| 2008/0161837 | A1 | 7/2008 | Toso et al. |
| 2008/0172071 | A1 | 7/2008 | Barker |
| 2008/0207989 | A1 | 8/2008 | Kaleta et al. |
| 2008/0208147 | A1 | 8/2008 | Argenta et al. |
| 2008/0312613 | A1 | 12/2008 | Heaton et al. |
| 2009/0012482 | A1 | 1/2009 | Pinto et al. |
| 2009/0062850 | A1 | 3/2009 | Ken |
| 2009/0076541 | A1 | 3/2009 | Chin et al. |
| 2009/0082792 | A1 | 3/2009 | Koyfman et al. |
| 2009/0088795 | A1 | 4/2009 | Cahill |
| 2009/0099519 | A1 | 4/2009 | Kaplan |
| 2009/0131892 | A1 | 5/2009 | Karpowicz et al. |
| 2009/0204130 | A1 | 8/2009 | Kantsevoy et al. |
| 2009/0216252 | A1 | 8/2009 | Melvin et al. |
| 2009/0228021 | A1 | 9/2009 | Leung |
| 2009/0234306 | A1 | 9/2009 | Vitaris |
| 2009/0240343 | A1 | 9/2009 | Adams |
| 2009/0312789 | A1 * | 12/2009 | Kassab et al. ................. 606/213 |
| 2010/0042144 | A1 * | 2/2010 | Bennett ......................... 606/213 |
| 2010/0298866 | A1 * | 11/2010 | Fischvogt ...................... 606/213 |

* cited by examiner

VACUUM PATCH FOR RAPID WOUND CLOSURE

CROSS-REFERENCE TO RELATED APPLICATIONS

This application claims the benefit of and priority to U.S. Provisional Patent Application No. 61/302,269, filed Feb. 8, 2010, the entire disclosure of which is incorporated by reference herein.

BACKGROUND

1. Technical Field

The present disclosure relates to systems and methods for wound closure. More particularly, the present disclosure relates to a surgical patch system for closing a wound during minimally invasive surgery.

2. Description of Related Art

Puncture wounds, wounds that pierce through tissue, may result from trauma or may be intentionally created in order to provide access to a body cavity during surgical procedures. During endoscopic surgical procedures, for example, a trocar device is utilized to puncture the peritoneum to provide an access port by way of a cannula through the abdominal wall. Generally, a trocar and/or cannula is placed through the abdominal wall for introduction of surgical instrumentation which is necessary to carry out the surgical procedure. In this manner, the surgeon may introduce a surgical instrument such as a grasper, scissor, clip applier, stapler or any other surgical instrument which may be necessary during the particular surgical procedure. Once the procedure is complete, it is necessary to close the wound.

Techniques for repairing wounds are widespread in medicine. Wound closure devices, such as sutures, staples, and other repair devices, like mesh or patch reinforcements, are frequently used for repair. Modern muscle reinforcement techniques may involve placement of an implant, such as a surgical mesh, near the injured tissue or defect to support the defect. The implant is either placed over the defect (anterior repair) or more often, under the defect (posterior repair).

SUMMARY

Accordingly, a surgical patch system for closing a wound includes a first surgical patch, a second surgical patch, a cord operably associated with the first and second surgical patches, and a port operably associated with the second surgical patch. The first surgical patch is positionable adjacent internal tissue of an underlying tissue site of an open wound. The second surgical patch is positionable adjacent external tissue relative to the underlying tissue site of the open wound. The external tissue is adjacent the internal tissue. The port is positioned to enable the application of negative pressure to the open wound.

The cord is mounted to the first surgical patch. The cord is configured and dimensioned to interconnect the first and second surgical patches. In embodiments, the cord may be a suture. The suture may be barbed. The cord, the first surgical patch, and/or the second surgical patch may include a bioactive agent.

The second surgical patch includes a cover feature adapted for contact with the open wound in order to promote fluid communication therebetween. The port includes a one-way valve. The one way valve is dimensioned to permit the reception and passage of the cord. The one way valve may be configured and dimensioned to engage an instrument configured and dimensioned to apply negative pressure to the open wound.

One or both of the first and second surgical patches includes a plurality of layers. One or more of the layers of one or both the first and second surgical patches is an adhesive layer. One or more of the layers of one or both the first and second surgical patches is an anti-adhesive layer. In embodiments, one or both of the first and second surgical patches may be bioabsorbable.

In one aspect, a surgical patch system for closing a wound includes a delivery tube configured and dimensioned to permit reception and passage of the first surgical patch into the underlying tissue site. The surgical patch system also includes an inner tube configured and dimensioned to pass the first surgical patch through the delivery tube into the underlying tissue site. The first surgical patch is repositionable between a closed condition for passage through the delivery tube and an open condition for mounting to the internal tissue of the underlying tissue site of the open wound.

In another aspect, a method for closing a wound includes advancing a first surgical patch having one or more cords mounted thereto into an underlying tissue site; affixing the first surgical patch to internal tissue of an open wound; affixing the one or more cords to a second surgical patch; affixing the second surgical patch to external tissue of the open wound; and applying negative pressure to at least one of the first and second surgical patches. One step includes threading the one or more cords through a one way valve mounted to the second surgical patch. The method includes inserting one or more of a hydrogel, an adhesive, and a bioactive agent into the open wound. The method also includes sealing the open wound while drawing blood and nutrients to the open wound via negative pressure through the one way valve mounted to the second surgical patch for further promoting the healing of the open wound.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

The present disclosure relates to devices, systems, and methods for minimally invasive surgeries such as, endoscopic, laparoscopic, arthroscopic, endoluminal and/or transluminal placement of one or more surgical patches at a surgical site. As used herein the term "surgical patch" is used to refer to any type of patch or mesh for use in surgical procedures, such as, for example, patches that can be attached to the abdominal wall. As used herein the term "laparoscopic deployment device" is used to refer to a deployment device that may be used during minimally invasive surgeries described above.

In the drawings and in the description that follows, the term "posterior," as is traditional, will refer to an area that is situated under, below, or behind the defect, while the term "anterior" will refer to an area that is situated over, above, or in front of the defect.

Laparoscopic surgical procedures are minimally invasive procedures that are carried out within the body cavity through use of access ports in conjunction with elongated surgical devices. An initial opening in the body tissue enables passage of the endoscopic or laparoscopic device to the interior of the body. Openings include natural passageways of the body or openings that are created by a tissue piercing device such as a trocar. During laparoscopic procedures, narrow punctures or incisions are made minimizing trauma to the body cavity and reducing patient recovery time. Although described herein with reference to laparoscopic surgery, the method may be applied to any type of surgery.

Figure 1:
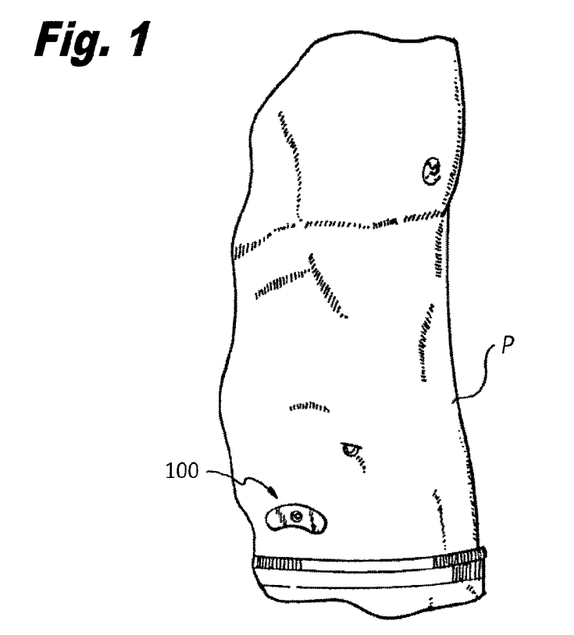
FIG. 1 is a view of one embodiment of a surgical patch system illustrated in situ in accordance with the principles of the present disclosure.
Figure 2:
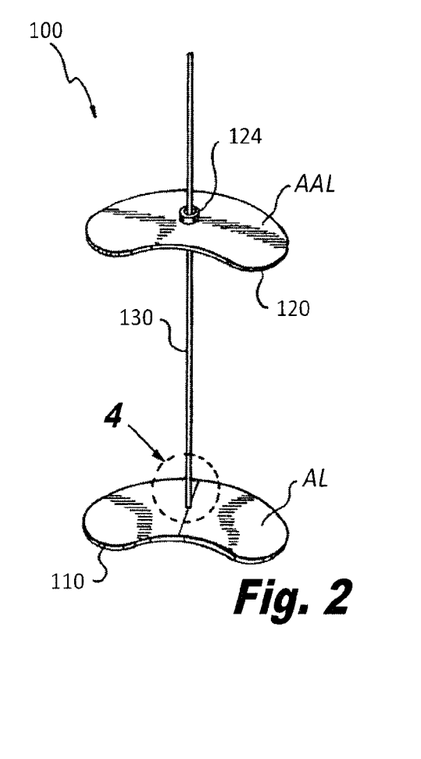
FIG. 2 is a top perspective view of the surgical patch system of FIG. 1.
Figure 3:
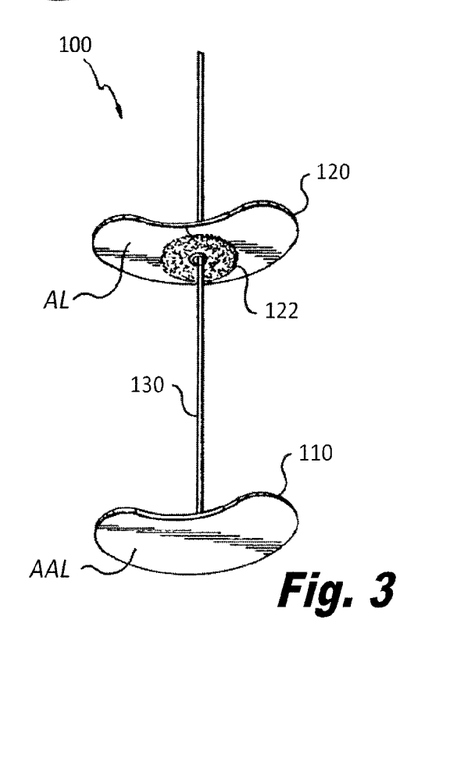
FIG. 3 is a bottom perspective view of the surgical patch system of FIG. 1.
Figure 6:
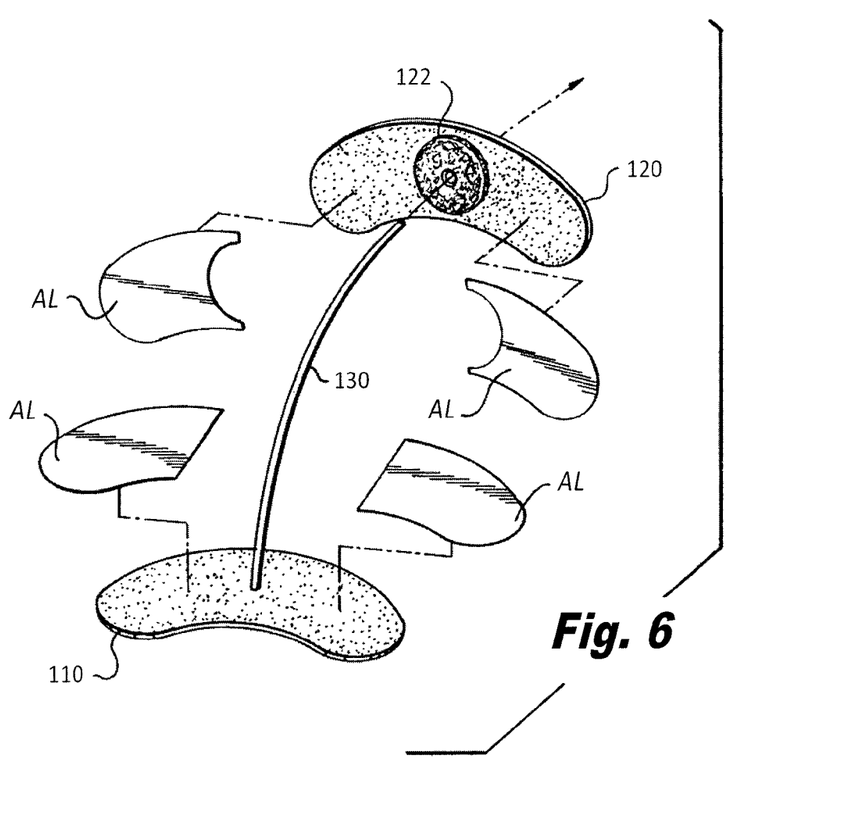
FIG. 6 is a perspective view, with parts separated, of the surgical patch system of FIG. 1.
Figures 7, 8:
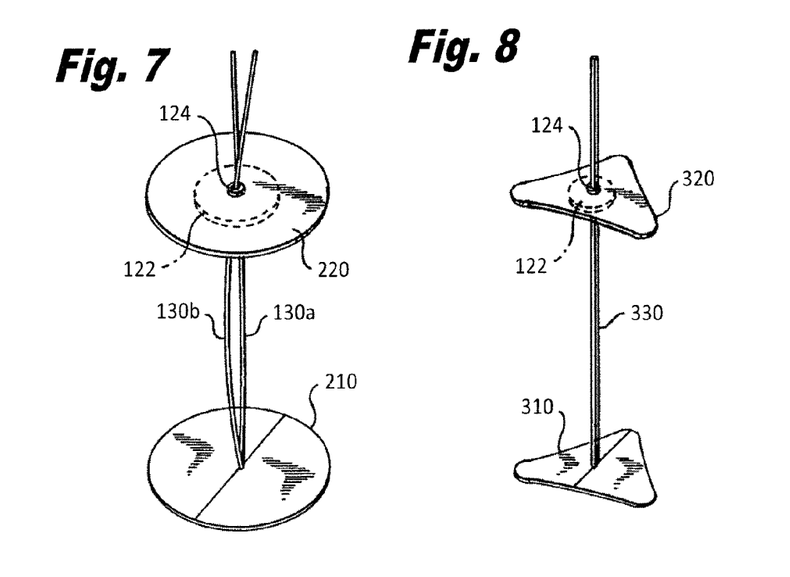
FIG. 7 is a top perspective view of an alternate embodiment of a surgical patch system in accordance with the present disclosure.
FIG. 8 is a top perspective view of yet another embodiment of the surgical patch system in accordance with the present disclosure.

Referring now in specific detail to the drawings, in which like numbers identify similar or identical elements, FIG. 1 shows one embodiment of a surgical patch system 100 for closing a wound "W" of a patient "P." From FIGS. 2-3, and 6, the surgical patch system 100 includes a first surgical patch 110 (posterior patch), a second surgical patch 120 (anterior patch), a cord 130 (or a plurality of cords 130a, 130b; see FIG. 7) operably associated with the first and second surgical patches 110, 120, and a port 124 operably associated with the second surgical patch 120 and positioned to enable the application of negative pressure to the wound "W." In certain embodiments, the cord 130 extends from the first surgical patch 110 and through the second patch 120. In embodiments, the surgical patch system 100 includes a delivery tube 140 (FIG. 9) (e.g., a laparoscopic deployment device) for inserting the first surgical patch 110 into an underlying tissue site "TS" of an open wound "W" (FIGS. 10-19). The delivery tube 140 is configured and dimensioned to permit reception and passage of the first surgical patch 110 into the underlying tissue site "TS." The surgical patch system 100 may also include an inner tube 150 (FIG. 11) configured and dimensioned to advance the first surgical patch 110 through the delivery tube 140 into the underlying tissue site "TS."

Figure 10:
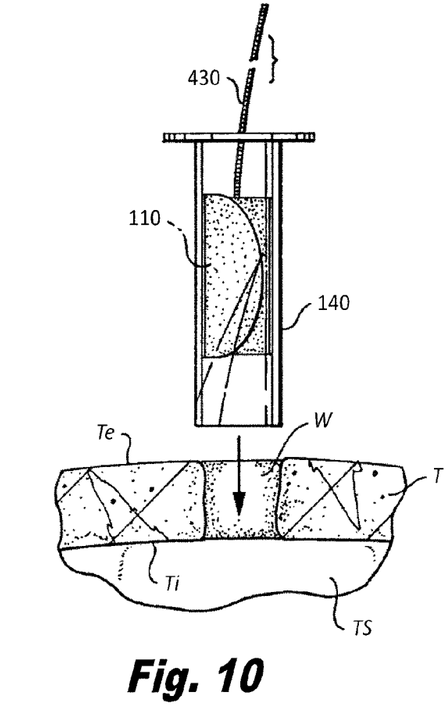
Figure 11:
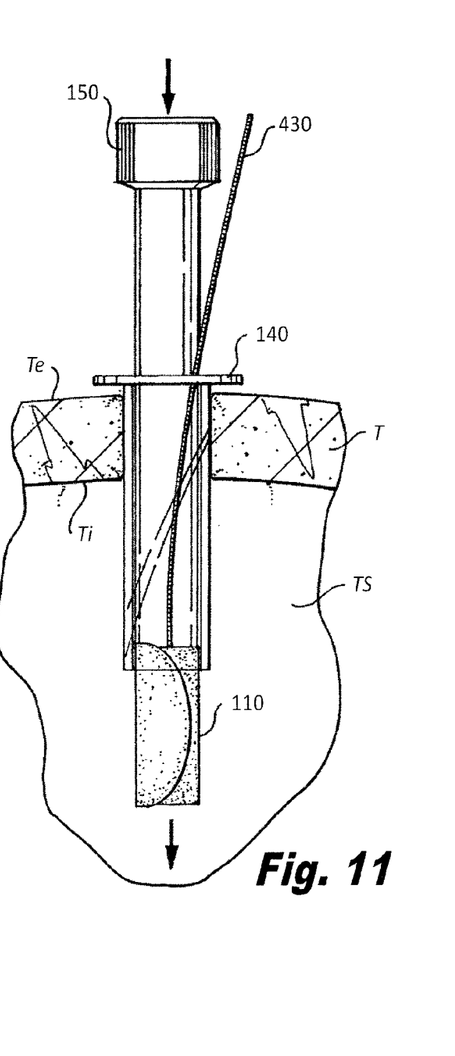
Figures 12, 13:
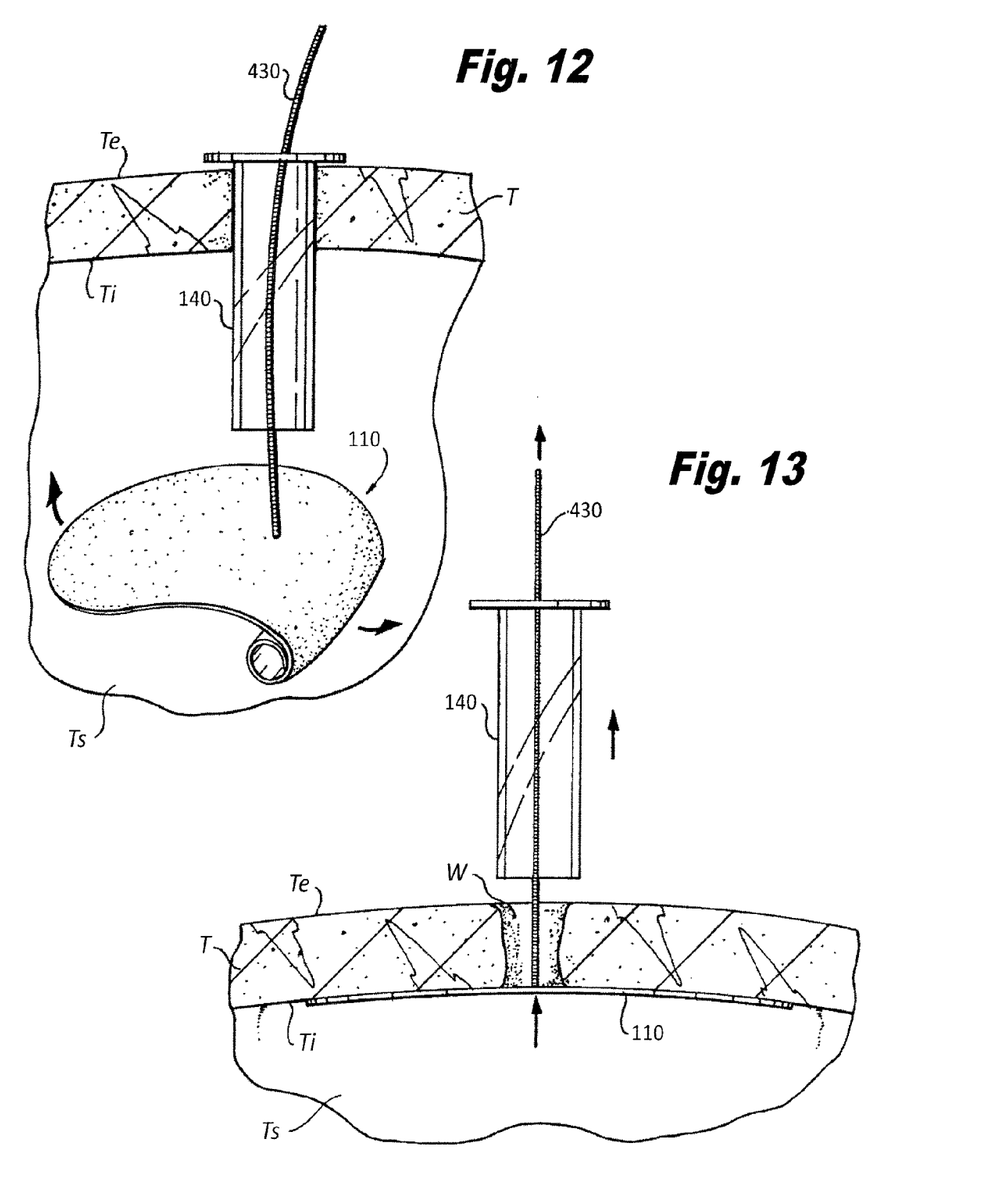
Figure 14:
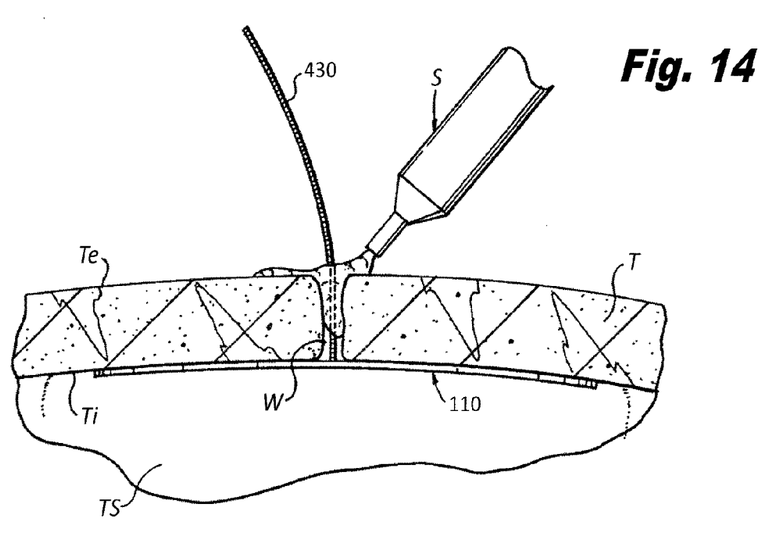
Figure 15:
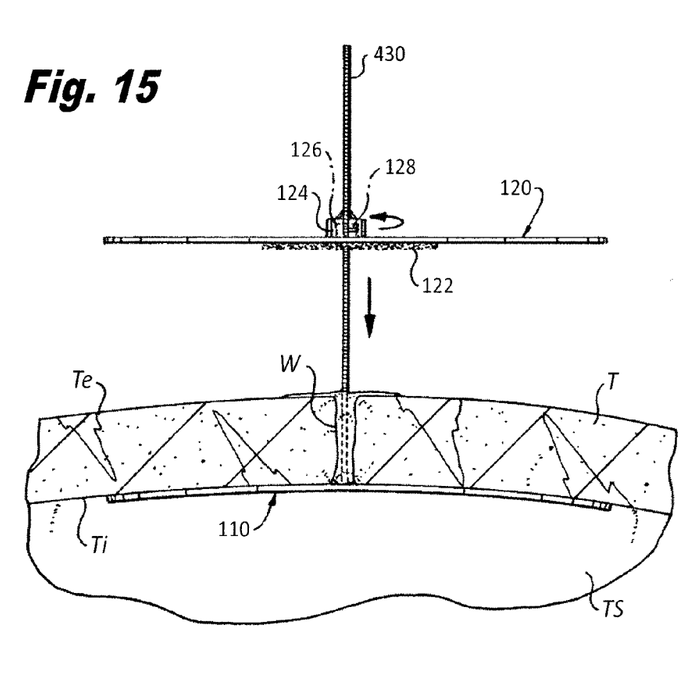
Figure 16:
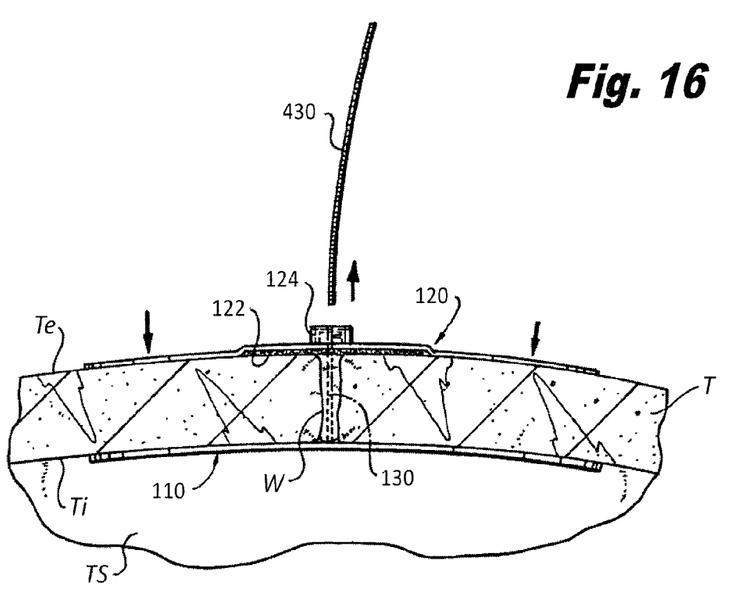

With continued reference to FIG. 10, the first surgical patch 110 is positionable adjacent internal tissue "Ti" of the underlying tissue site "TS" of the open wound "W." From FIGS. 15-16, the second surgical patch 120 is positionable adjacent external tissue "Te" relative to the underlying tissue site "TS" of the open wound "W." The external tissue "Te" is adjacent the internal tissue "Ti." The first and second surgical patches 110, 120 appose the open wound "W" when positioned adjacent the open wound "W" in order to facilitate healing thereof.

Figure 4:
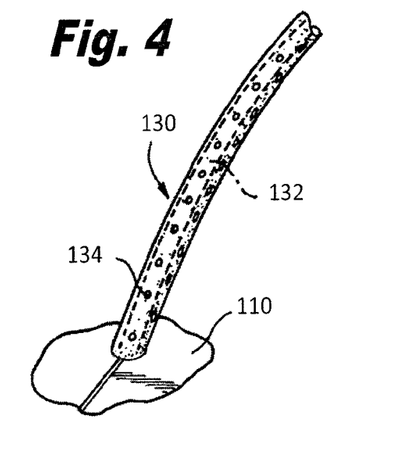
FIG. 4 is an enlarged perspective view of the detailed area delineated in FIG. 2.
Figure 5:
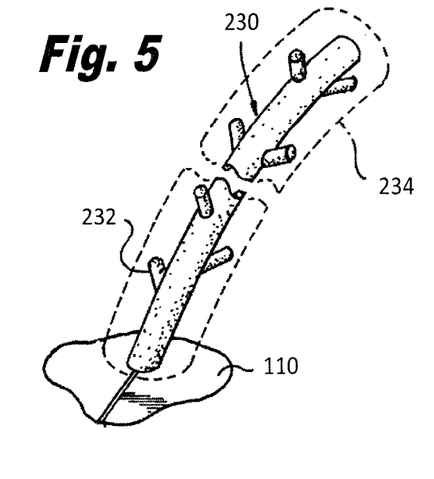
FIG. 5 is a perspective view of an alternate embodiment of a portion of the cord of the surgical patch system of FIG. 1.

The cord 130 may be mounted to either of the first surgical patch 110 and/or the second surgical patch 120. In certain embodiments, the cord 130 may be integrally formed with the first surgical patch 110 or may be mounted thereto (e.g., fastened, tied-off, adhered, etc.) The cord 130 is configured and dimensioned to interconnect the first and second surgical patches 110, 120. The cord 130 may define a lumen therethrough 132 and may include perforations 134 for permitting passage of fluids (e.g., bioactive agents, adhesives, etc. described in greater detail hereinbelow) therethrough (see FIG. 4). As illustrated in FIG. 5, one embodiment of a cord 230 includes barbs 232 which extend outward from a central axis of the cord 230. The angle and geometry of the barbs 232 may vary. This embodiment may further include a removable sheath 234 positionable over the barbs 232 in order to facilitate the passage of the cord 230 through the second surgical patch 120. In another embodiment, shown in FIG. 8, a cord 330 may be a suture or a plurality of sutures. Additionally, the length and cross-sectional shape and dimensions of the cord may vary according to procedure. Further still, a cord 430 may include threading 432 (FIG. 9) in order to facilitate a threaded interaction with the port 124, which may also be threaded.

Each surgical patch 110, 120 may be any type of surgical patch for use in tissue repair and suitable for use in situ. Each surgical patch 110, 120 may be any suitable shape. For example, alternative embodiments of surgical patch systems may include circular (FIG. 7: first and second surgical patches 210, 220) and/or noncircular surgical patches (FIG. 8: first and second surgical patches 310, 320). Each surgical patch 110, 120 may be any shape or size suitable for covering a herniated or incised area and securing each surgical patch 110, 120 to surrounding tissue. Each surgical patch 110, 120 may be preformed to a certain size, such as, for example, a 9 cm diameter round surgical patch or 50 cm×50 cm square surgical patch. In embodiments, each surgical patch 110, 120 and/or the cord 130 may be cut to a particular size and shape as needed, accommodating different patients or procedures.

During laparoscopic surgery, each surgical patch 110, 120 may also be rolled, folded, or otherwise oriented in order to form a shape more appropriate for transfer through any suitable laparoscopic device known in the art. Furthermore, each surgical patch 110, 120 and/or the cord 130 may be made of multiple fibers, or may be made of a single fiber. The fibers may be a monofilament or multi-filament.

Suitable polymers which may be used to construct implants disclosed herein include, for example, synthetic materials, natural materials (e.g., biological) and combinations thereof. Suitable materials include, polyolefins such as polyethylene (including ultra high molecular weight polyethylene) and polypropylene including atactic, isotactic, syndiotactic, and blends thereof; polyethylene glycols; polyethylene oxides; ultra high molecular weight polyethylene; copolymers of polyethylene and polypropylene; polyisobutylene and ethylene-alpha olefin copolymers; fluorinated polyolefins such as fluoroethylenes, fluoropropylenes, fluoroPEGSs, and polytetrafluoroethylene; polyamides such as nylon, Nylon 6, Nylon 6,6, Nylon 6,10, Nylon 11, Nylon 12, and polycaprolactam; polyamines; polyimines; polyesters such as polyethylene terephthalate, polyethylene naphthalate, polytrimethylene terephthalate, and polybutylene terephthalate; polyethers; polybutester; polytetramethylene ether glycol; 1,4-butanediol; polyurethanes; acrylic polymers; methacrylics; vinyl halide polymers and copolymers, such as polyvinyl chloride; polyvinyl alcohols; polyvinyl ethers such as polyvinyl methyl ether; polyvinylidene halides such as polyvinylidene fluoride and polyvinylidene chloride; polychlorofluoroethylene; polyacrylonitrile; polyaryletherketones; polyvinyl ketones; polyvinyl aromatics such as polystyrene; polyvinyl esters such as polyvinyl acetate; copolymers of vinyl monomers with each other and olefins, such as ethylene-methyl methacrylate copolymers; acrylonitrile-styrene copolymers; ABS resins; ethylene-vinyl acetate copolymers; alkyd resins; polycarbonates; polyoxymethylenes; polyphosphazine; polyimides; epoxy resins; aramids; rayon; rayon-triacetate; spandex; silicones; and copolymers and combinations thereof. Additionally, non-biodegradable polymers and monomers may be combined with each other to create a core of a fiber, for example a fiber possessing a core-sheath configuration.

Additionally, biodegradable synthetic or natural materials may be employed. As used herein, the term "biodegradable" includes both bioabsorbable and bioresorbable materials. By biodegradable, it is meant that the materials decompose, or lose structural integrity under body conditions (e.g., enzymatic degradation, hydrolysis) or are broken down (physically or chemically) under physiologic conditions in the body (e.g., dissolution) such that the degradation products are excretable or absorbable by the body.

Suitable bioabsorbable polymers may comprise implants of the present disclosure that include, but are not limited to polymers selected from the group consisting of aliphatic polyesters; polyamides; polyamines; polyalkylene oxalates; poly(anhydrides); polyamidoesters; copoly(ether-esters); poly(carbonates) including tyrosine derived carbonates; poly(hydroxyalkanoates) such as poly(hydroxybutyric acid), poly(hydroxyvaleric acid), and poly(hydroxybutyrate); polyimide carbonates; poly(imino carbonates) such as such as poly(bisphenol A-iminocarbonate and the like); polyorthoesters; polyoxaesters including those containing amine groups; polyphosphazenes; poly(propylene fumarates); polyurethanes; polymer drugs such as polydiflunisol, polyaspirin, and protein therapeutics; biologically modified (e.g., protein, peptide) bioabsorbable polymers; and copolymers, block copolymers, homopolymers, blends, and combinations thereof.

More specifically, for the purpose of this invention, aliphatic polyesters include, but are not limited to, homopolymers and copolymers of lactide (including lactic acid, D-,L- and meso lactide); glycolide (including glycolic acid); epsilon-caprolactone, p-dioxanone (1,4-dioxan-2-one); trimethylene carbonate (1,3-dioxan-2-one); alkyl derivatives of trimethylene carbonate; Δ-valerolactone; β-butyrolactone; γ-butyrolactone; ε-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; α,α diethylpropiolactone; ethylene carbonate; ethylene oxalate; 3-methyl-1,4-dioxane-2,5-dione; 3,3-diethyl-1,4-dioxan-2,5-dione; 6,8-dioxabicycloctane-7-one; and polymer blends and copolymers thereof.

Other suitable biodegradable polymers include but are not limited to poly(amino acids) including proteins such as collagen (I, II and III), elastin, fibrin, fibrinogen, silk, and albumin; peptides including sequences for laminin and fibronectin (RGD); polysaccharides such as hyaluronic acid (HA), dextran, alginate, chitin, chitosan, and cellulose; glycosaminoglycan; gut; and combinations thereof. Collagen as used herein includes natural collagen such as animal derived collagen, gelatinized collagen, or synthetic collagen such as human or bacterial recombinant collagen.

Additionally, synthetically modified natural polymers such as cellulose and polysaccharide derivatives, including alkyl celluloses, hydroxyalkyl celluloses, cellulose ethers, cellulose esters, nitrocelluloses, and chitosan may be utilized. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose (CMC), cellulose triacetate, and cellulose sulfate sodium salt. These may be collectively referred to herein, in embodiments, as "celluloses."

Additionally, the surgical device may comprise any or all of emulsifying agents, solubilizing agents, wetting agents, plasticizers, active agents, water soluble inert fillers, preservatives, buffering agents, coloring agents, and stabilizers. Addition of a plasticizer to the formulation can improve flexibility. The plasticizer or mixture of plasticizers may be polyethylene glycol, glycerol, sorbitol, sucrose, corn syrup, fructose, dioctyl-sodium sulfosuccinate, triethyl citrate, tributyl citrate, 1,2-propylenglycol, mono-, di- or triacetates of glycerol, or natural gums.

Each surgical patch 110, 120 and/or the cord 130 may be formed using any method suitable to forming surgical patch structures, including but not limited to knitting, weaving, non-woven techniques, lyophilization and the like. Suitable techniques for making each surgical patch 110, 120 and/or the cord 130 are within the purview of those skilled in the art.

The surgical patch system 100 may include a bioactive agent. The term "bioactive agent," as used herein, is used in its broadest sense and includes any substance or mixture of substances that have clinical use. Consequently, bioactive agents may or may not have pharmacological activity per se, e.g., a dye. Alternatively a bioactive agent could be any agent that provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the each surgical patch 110, 120 and/or the cord 130 in any suitable form, e.g., films, powders, liquids, gels, and the like.

Examples of non-limiting classes of bioactive agents, which may be utilized in accordance with the present disclosure include: anti-adhesives; antimicrobials; analgesics; antipyretics; anesthetics; antiepileptics; antihistamines; anti-inflammatories; cardiovascular drugs; diagnostic agents; sympathomimetics; cholinomimetics; antimuscarinics; antispasmodics; hormones; growth factors; muscle relaxants; adrenergic neuron blockers; antineoplastics; immunogenic agents; immunosuppressants; gastrointestinal drugs; diuretics; steroids; lipids; nucleic acids (DNA, RNA) lipopolysaccharides; polysaccharides; platelet activating drugs; clotting factors; and enzymes. It is also intended that combinations of bioactive agents may be used.

In certain embodiments, anti-adhesive agents can be used to prevent adhesions from forming between at least one surface of the surgical patch 110 and/or the cord 130 and the surrounding tissues opposite the target tissue (see FIG. 3). In addition, anti-adhesive agents may be used to prevent adhesions from forming between the coated implantable medical device and the packaging material. Some examples of these agents include, but are not limited to hydrophilic polymers such as polyethylene glycol, polypropylene glycol, glycerol, polysaccharides such as hyaluronic acid, polyethylene oxide, and combinations thereof.

Suitable antimicrobial agents which may be included as a bioactive agent include: antimicrobial proteins and peptides such as bovine lactoferrin and lactoferricin B; cationic peptides, and metal-chelating peptides; phospholipid copolymers including phosphoryl choline containing polymers; triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate; silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine; polymyxin; tetracycline; aminoglycosides, such as tobramycin and gentamicin; rifampicin; bacitracin; neomycin; chloramphenicol; miconazole; quinolones such as oxolinic acid, norfloxacin, nalidixic acid, pefloxacin, enoxacin and ciprofloxacin; penicillins such as oxacillin and pipracil, nonoxynol 9, fusidic acid, cephalosporins; and combinations thereof.

Other bioactive agents, which may be included as a bioactive agent include local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents, such as coronary vasodilators and nitroglycerin; alkaloids; analgesics; narcotics such as codeine, dihydrocodeinone, meperidine, morphine and the like; non-narcotics, such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents, such as hormonal agents, hydrocortisone, prednisolone, prednisone, non-hormonal agents, allopurinol, indomethacin, phenylbutazone and the like; prostaglandins and cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable bioactive agents, which may be included in the surgical patch system 100 of the present disclosure include: viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons (β-IFN, α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids, such as antisense molecules, DNA, RNA, RNAi; oligonucleotides; polynucleotides; and ribozymes.

Other bioactive agents which may be utilized in accordance with the present disclosure include drugs, amino acids, peptides, polypeptides, proteins, polysaccharides, muteins, immunoglobulins, antibodies, cytokines (e.g., lymphokines, monokines, chemokines), blood clotting factors, hemopoietic factors, interleukins (1 through 18), interferons (β-IFN, α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone, luteinizing hormone releasing factor), vaccines (e.g., tumoral, bacterial and viral antigens); somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi; oligonucleotides; polynucleotides; cells, viruses, and ribozymes.

One or both surgical patches 110, 120 may include a cover feature 122 centrally secured thereto. Each surgical patch 110, 120 may be adapted for contact with the open wound "W" in order to promote fluid communication therebetween and may be adapted to resist adhesion to the open wound "W," but in embodiments, may adhere to the tissue surface "Te." The cover feature 122 may be formed of a textile, sponge, foam, porous, absorbent material or any combination thereof to enable the absorption of fluids and/or the passage of fluids therethrough. Similarly, the cover feature 122 may comprise and open or closed cell foam. In this manner, the cover feature 122 may absorb fluid emanating from the open wound "W," create hemostasis, or provide fluid (e.g., growth factors, etc.) to the open wound "W." As best shown in FIG. 15, the port 124, which is operably connected with the surgical patch 120 and may be mounted to the cover feature 122, may include a one-way valve 126. The one-way valve 126 may be dimensioned to permit the reception and passage of the cord 130. The cord 130 may pass through port 124 of the second surgical patch 120 adjacent the one-way valve 126. In embodiments of the surgical patch system 100 including cord 430, the cord 430 may be threaded through the port 124, as described above. The port 124 is configured and dimensioned to engage an instrument configured and dimensioned to apply negative pressure to the open wound "W", e.g., a syringe (see FIG. 14). As shown in FIG. 15, the port 124 may include a ratchet mechanism 128 that may enable the second surgical patch 120 to be ratcheted distally across the cord (e.g., via the perforations 134 and/or threading 432) so that the second surgical patch 120 sequentially moves into approximation with the first surgical patch 110. In this manner, the ratchet mechanism 128 substantially prevents proximal movement of the second surgical patch 120.

From FIGS. 2, 3 and 6, one or both of the first and second surgical patches 110, 120 may be formed of laminate construction and include one or more layers. One or more of the layers of one or both the first and second surgical patches 110, 120 may be an adhesive layer "AL" (see FIG. 6). One or more of the layers of one or both the first and second surgical patches 110, 120 may be an anti-adhesive layer "AAL" configured to resist adhesion to the tissues "T" (e.g., bowel). Each layer may be positioned onto one or both of the first and second surgical patches 110, 120 by means of an adhesive film or coating.

Figure 9:
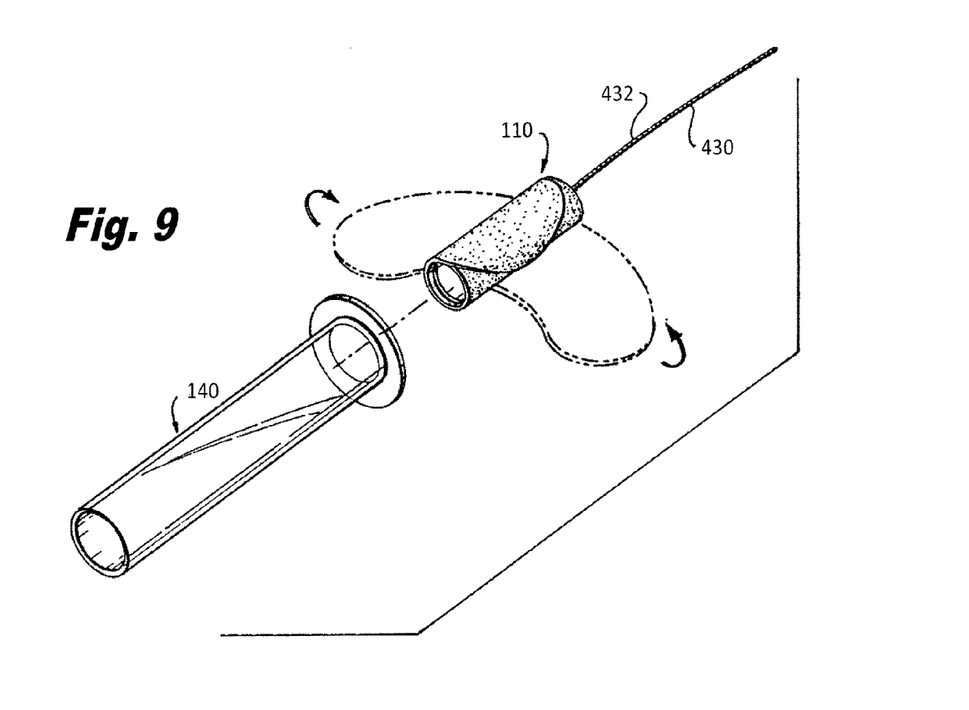
FIGS. 9-17 are progressive views illustrating methods for placing the surgical patch system of FIG. 1 at a surgical site in accordance with the principles of the present disclosure.

In operation, the first surgical patch 110 is repositionable from an open condition to a closed condition (e.g., rolled, folded, etc.) for passage through the delivery tube 140 (see FIG. 9). The first surgical patch 110 may then be advanced through the delivery tube 110 via the inner tube 150. With one or more cords 130 being mounted to the first surgical patch 110, the first surgical patch 110 is repositioned into the open condition (FIG. 12) upon being deployed from the delivery tube 140 into the underlying tissue site "TS." In this manner, the first surgical patch 110 is positioned into the open position which may be in response to the opposing forces resulting from the advancement (including the inner tube advancement and gravity) and the force of the cord 130 (held by a physician or instrument such as a grasper [not shown]). In alternate embodiments, shape memory materials may be employed in the first surgical patch 110, controlling and attributing to the unfolding or unrolling of the first surgical patch 110 in situ. Shape memory materials may include, but are not limited to, those which respond to external stimulus such as heat or temperature. The one or more cords 130 are then moved proximally so that the first surgical patch 110 is positioned adjacent the internal tissue "Ti" of the underlying tissue site "TS" of the open wound "W." In some embodiments, an adhesive layer "AL" may then be adhered to the internal tissue "Ti" (e.g., peritoneum). The physician may then insert one or more of a hydrogel, an adhesive, a plug, a bioactive agent, etc. into the open wound to further seal or promote healing of the open wound "W," (e.g., via a syringe—see FIG. 14). In embodiments in which the one or more cords 130 define a lumen 132 and/or perforations 134 (see FIG. 4), fluids (e.g., bioactive agents) may be passed therethrough for further sealing or promoting healing of the open wound "W."

Figure 17:
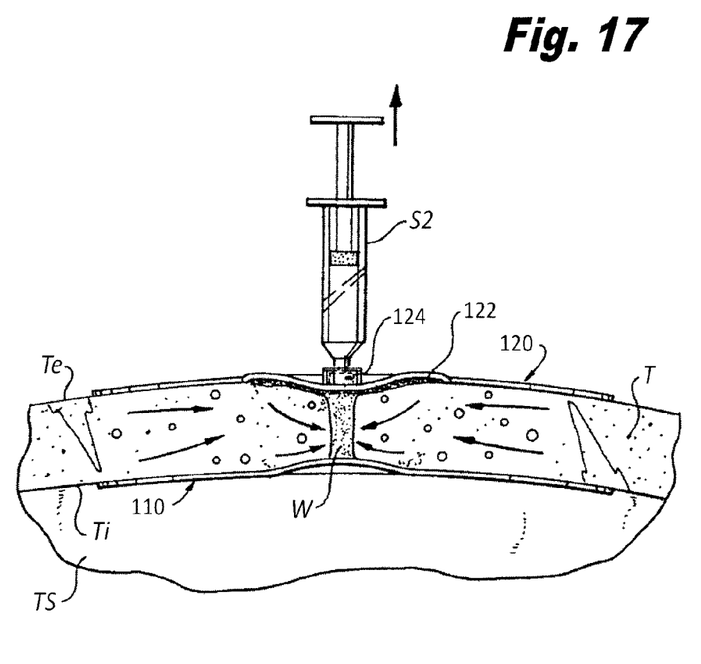
Figure 18:
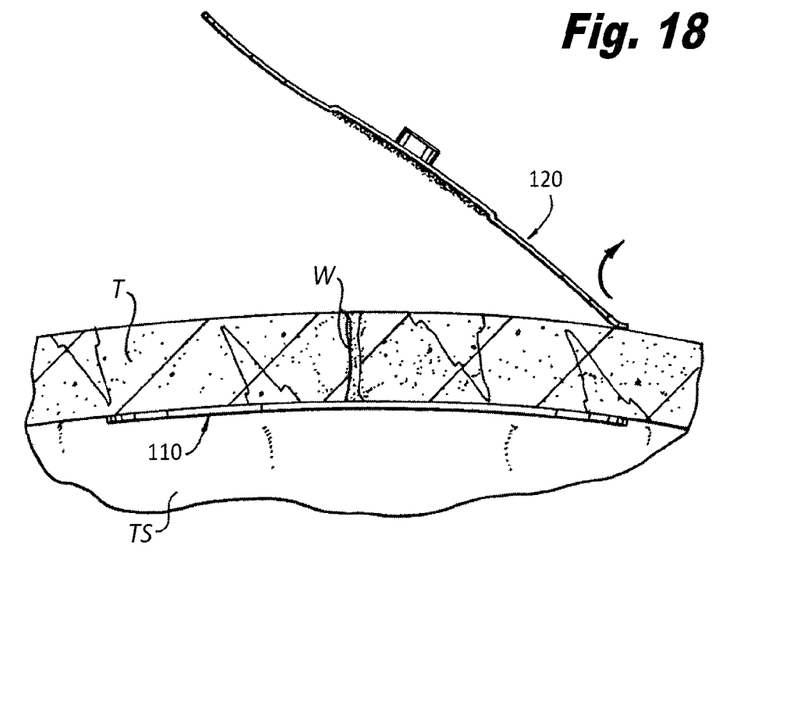
FIG. 18-19 are side views in partial cross section illustrating methods for removing embodiments of the surgical patch system from the surgical site in accordance with the present disclosure.
Figure 19:
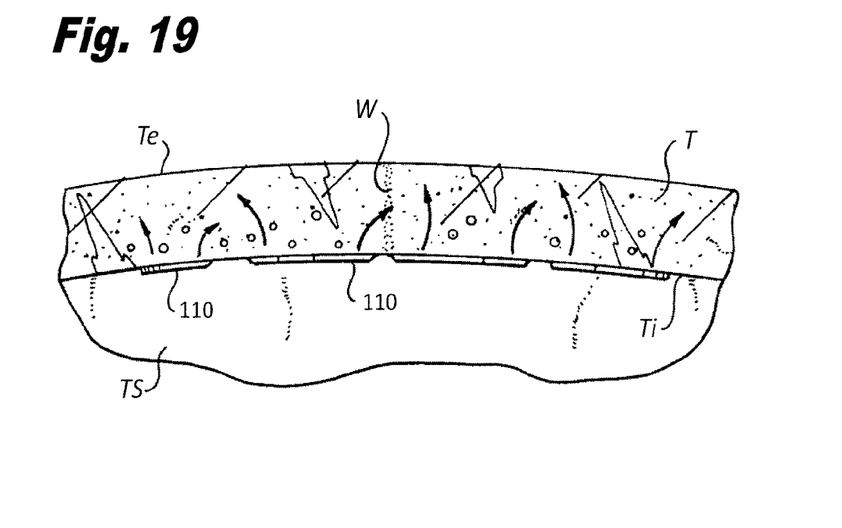

As illustrated in FIG. 15, the one or more cords 130 may then be passed (or threaded and/or ratcheted) through the one way valve 124 such that the second surgical patch 120 may be advanced distally across the one or more cords 130 while tensile counter pressure is applied from the cord 130 and the first surgical patch 110 which engages the internal tissue "Ti," e.g., the peritoneum in response to proximal retraction forces applied to the cord 130 from the physician. In this respect, the first and second surgical patches 110, 120 approximate toward one another and sandwich the tissue "T" therebetween. In this manner, one or more of the adhesive layers "AL" of one or both of the first and second surgical patches 110, 120 forms a hermetic seal with the tissue "T." The one or more cords 130 may then be mounted or positionally fixed (e.g., fastened, tied off, etc.) to the second surgical patch 120 for maintaining the first and second surgical patches 110, 120 affixed to the open wound "W." As such, the first surgical patch 110 is positioned adjacent to the internal tissue "Ti" and the second surgical patch 120 is positioned adjacent to the external tissue "Te" of the open wound "W" in order to facilitate the healing of the open wound "W." As illustrated in FIG. 17, a syringe "S2" or similar device may be removably connected to the port 124, e.g., by means of a luer lock or other similar mechanical connection known in the art. In this manner, the physician may use the syringe to seal the open wound "W" while drawing blood and nutrients to the open wound "W" through negative pressure. After dermal closure and primary healing of the open wound "W," the second surgical patch 120 may be removed (FIG. 18) in a manner typical with standard adhesive bandages. The internal components, i.e., the first surgical patch 110 and the portions of cord positioned within the body, may be absorbable by the body (FIG. 19).

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical patch system for closing a wound, comprising:
    a first surgical patch positionable adjacent internal tissue of an underlying tissue site of an open wound;
    a second surgical patch positionable adjacent external tissue relative to the underlying tissue site of the open wound, the external tissue being adjacent the internal tissue;
    a cord operably associated with the first and second surgical patches, the cord configured and dimensioned to interconnect the first and second surgical patches;
    a port operably associated with the second surgical patch and positioned to enable the application of negative pressure to the open wound, wherein the port includes a one-way valve; and
    a vacuum source selectively securable to the port and dimensioned to apply negative pressure between the first and second surgical patches to seal the open wound between the first and second surgical patches.

2. The surgical patch system of claim 1 wherein at least one of the first and second surgical patches includes a plurality of layers.

3. The surgical patch system of claim 2 wherein at least one of the layers of at least one of the first and second surgical patches is an adhesive layer.

4. The surgical patch system of claim 2 wherein at least one of the layers of at least one of the first and second surgical patches is an anti-adhesive layer.

5. The surgical patch system of claim 2 wherein the cord is a suture.

6. The surgical patch system of claim 5 wherein the suture is barbed.

7. The surgical patch system of claim 1 wherein the second surgical patch includes a cover feature adapted for contact with the open wound in order to promote fluid communication therebetween.

8. The surgical patch system of claim 1 wherein at least one of the cord, the first surgical patch, and the second surgical patch includes a bioactive agent.

9. The surgical patch system of claim 1 wherein the cord is mounted to the first surgical patch.

10. The surgical patch system of claim 1 wherein the one way valve is dimensioned to permit the reception and passage of the cord.

11. The surgical patch system of claim 1 wherein the one way valve is configured and dimensioned to permit the vacuum source to apply negative pressure through the port and to the open wound when the vacuum source is secured to the port.

12. The surgical patch system of claim 1 wherein the first surgical patch secures to the internal tissue and bioabsorbs after a predetermined period of time, and wherein the second surgical patch secures to the external tissue via an adhesive to enable the second surgical patch to be non-invasively and selectively removable from the external tissue.

13. A surgical patch system for closing a wound, comprising:
    a first surgical patch positionable adjacent internal tissue of an underlying tissue site of an open wound;
    a second surgical patch positionable adjacent external tissue relative to the underlying tissue site of the open wound, the external tissue being adjacent the internal tissue;
    a delivery tube configured and dimensioned to permit reception and passage of the first surgical patch into the underlying tissue site;

a cord operably associated with the first and second surgical patches, the cord configured and dimensioned to interconnect the first and second surgical patches;

a port operably associated with the second surgical patch and positioned to enable the application of negative pressure to the open wound, wherein the port includes a one-way valve; and a vacuum source selectively securable to the port and dimensioned to apply negative pressure between the first and second surgical patches to seal the open wound between the first and second surgical patches.

14. The surgical patch system of claim 13 further comprising an inner tube configured and dimensioned to pass the first surgical patch through the delivery tube into the underlying tissue site.

15. The surgical patch system of claim 13 wherein the first surgical patch is repositionable between a closed condition for passage through the delivery tube and an open condition for mounting to the internal tissue of the underlying tissue site of the open wound.

16. The surgical patch system of claim 13 wherein the vacuum source includes a syringe.

17. The surgical patch system of claim 16, wherein the syringe and port are selectively mechanically secured to each other via a luer lock arrangement.

18. A surgical patch system for closing a wound, comprising:

a first surgical patch positionable adjacent internal tissue of an underlying tissue site of an open wound;

a second surgical patch positionable adjacent external tissue relative to the underlying tissue site of the open wound, the external tissue being adjacent the internal tissue;

a cord operably associated with the first and second surgical patches, the cord configured and dimensioned to interconnect the first and second surgical patches;

a port defining an opening, the port fixedly secured to the second surgical patch and extending from an outer surface of the second surgical patch, the port including a one-way valve that extends from an inner surface of the port into the opening to block the opening, the one-way valve being movable in response to a passage of the cord through the opening and being movable in response to passage of negative pressure through the opening; and a vacuum source securable to the port to apply negative pressure through the one-way valve to seal the open wound between the first and second surgical patches.

* * * * *